(12) United States Patent
Mathews et al.

(10) Patent No.: US 8,694,269 B2
(45) Date of Patent: Apr. 8, 2014

(54) REDUCING THE RINGING OF ACTUATOR ELEMENTS IN ULTRASOUND BASED HEALTH MONITORING SYSTEMS

(75) Inventors: V. John Mathews, Salt Lake City, UT (US); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 636 days.

(21) Appl. No.: 12/189,423

(22) Filed: Aug. 11, 2008

(65) Prior Publication Data

US 2010/0036618 A1 Feb. 11, 2010

(51) Int. Cl.
*G06F 19/00* (2011.01)
*G01R 23/02* (2006.01)

(52) U.S. Cl.
CPC ..................... *G01R 23/02* (2013.01)
USPC .......................................................... 702/35

(58) Field of Classification Search
USPC .......................................................... 702/35
See application file for complete search history.

(56) References Cited

U.S. PATENT DOCUMENTS

| | | | |
|---|---|---|---|
| 6,006,163 A | 12/1999 | Lichtenwalner et al. | |
| 6,484,132 B1 | 11/2002 | Hively et al. | |
| 6,958,686 B2 | 10/2005 | Okubo | |
| 7,000,478 B1 | 2/2006 | Zwollo et al. | |
| 7,061,229 B2 | 6/2006 | Townsend et al. | |
| 7,286,964 B2 | 10/2007 | Kim | |
| 7,324,193 B2 | 1/2008 | Lally et al. | |
| 7,374,539 B2 | 5/2008 | Fernando et al. | |
| 7,487,059 B2 | 2/2009 | Davis et al. | |
| 7,498,576 B2 | 3/2009 | Micko | |
| 7,552,027 B2 | 6/2009 | Kearns et al. | |
| 7,720,626 B2 | 5/2010 | Mathews | |
| 7,726,875 B2 | 6/2010 | Yuhas | |
| 7,822,573 B2 | 10/2010 | Ihn | |
| 7,842,874 B2 | 11/2010 | Jehan | |
| 7,937,248 B2 | 5/2011 | Ihn et al. | |
| 7,991,587 B2 | 8/2011 | Ihn | |
| 8,055,455 B2 | 11/2011 | Ihn et al. | |
| 8,127,610 B2 | 3/2012 | Mathews | |
| 2007/0291958 A1* | 12/2007 | Jehan ............................ 381/103 |
| 2008/0319692 A1* | 12/2008 | Davis et al. .................... 702/76 |
| 2009/0083004 A1 | 3/2009 | Ihn et al. | |
| 2010/0036617 A1 | 2/2010 | Mathews | |

OTHER PUBLICATIONS

Gyuhae Park, Eric Ruggiero, Marion Sausse and Daniel J. Inman, Vibration Testing and Analysis of Inflatable Structures Using Smart Materials, Proceedings of 2001 ASME International Mechanical Engineering Congress and Exposition Nov. 11-16, 2001, New York, NY, p. 1-8.*

Jerome P. Lynch, Design of a Wireless Active Sensing Unit for Structural Health Monitoring, Source: SPIE 11th Annual International Symposium on Smart Structures and Materials, San Diego, CA, USA, Mar. 14-18, 2004, 12 pages.*

PCB Piezotronics, "Installation Drawing, Model 352C22, Accelerometer," Drawing No. 10600, Mar. 26, 2003, 2 sheets.

(Continued)

*Primary Examiner* — Tung S Lau
(74) *Attorney, Agent, or Firm* — Yee & Associates, P.C.

(57) ABSTRACT

A method and apparatus are present for monitoring a structure. A signal is sent into the structure, wherein the signal has a limited duration and a varying frequency. A response to the signal is received and the response is compared to a baseline to form a comparison.

9 Claims, 6 Drawing Sheets

(56) References Cited

OTHER PUBLICATIONS

PCB Piezotronics, "Model 352C22 Spec Sheet," 2 pages, accessed Nov. 3, 2011, http://pcb.com/spec_sheet.asp?model_352C22.

Measurement Specialties, Inc., "Vibration Sensor (SDT1-028K)," Instruction Sheet 408-9945, Rev. G, Oct. 27, 1998, 2 pages.

UK Intellectual Property Office Search Report, dated Nov. 6, 2008, regarding Application No. GB0812572.6, 3 pages.

Croxford et al., "Strategies for Overcoming the Effect of Temperature on Guided Wave Structural Health Monitoring", Proceedings of the SPIE Conference on Health Monitoring and Smart Nondestructive Evaluation of Structural and Biological Systems III, vol. 6532, Mar. 2007, pp. 6531T-1-6531T-10.

Kovvali et al., "Time-Frequency based Classification of Structural Damage", Proceedings of 48th AIAA/ASME/ASCE/AHS/ASC Structures, Structural Dynamics, and Materials Conference, Apr. 2007, 11 pages.

Leonard et al., "Ultrasonic Lamb wave tomography", Inverse Problems, vol. 18, No. 6, Dec. 2002, pp. 1795-1808.

Leutenegger et al., "Detection of defects in cylindrical structures using a time reverse method and a finite-difference approach", Ultrasonics, vol. 40, Issue 10, May 2002, pp. 721-725.

Leutenegger et al., "Non-destructive testing of tubes using a time reverse numerical simulation (TRNS) method", Ultrasonics, vol. 41, May 2004, pp. 811-822.

Park et al., "Overview of Piezoelectric Impedance-Based Health Monitoring and Path Forward," The Shock and Vibration Digest, vol. 35, No. 6, Nov. 2003, pp. 451-463.

Prasad et al., "Structural health monitoring of composite structures using Lamb wave tomography", Smart Materials and Structures, vol. 13, No. 5, Oct. 2004, pp. N73-N79.

Wang et al., "A synthetic time-reversal imaging method for structural health monitoring", Smart Materials and Structures, vol. 13, No. 2, Apr. 2004, pp. 415-423.

Office Action, dated Nov. 4, 2009, regarding USPTO U.S. Appl. No. 11/840,427, 12 pages.

Notice of Allowance, dated Feb. 19, 2010, regarding USPTO U.S. Appl. No. 11/840,427, 8 pages.

Office Action, dated Apr. 22, 2010, regarding USPTO U.S. Appl. No. 11/840,427, 12 pages.

Notice of Allowance, dated Jun. 16, 2010, regarding USPTO U.S. Appl. No. 11/840,427, 9 pages.

Office Action, dated Sep. 23, 2010, regarding USPTO U.S. Appl. No. 12/851,408, 15 pages.

Notice of Allowance, dated Mar. 21, 2011, regarding USPTO U.S. Appl. No. 12/851,408, 7 pages.

Office Action, dated Aug. 3, 2010, regarding USPTO U.S. Appl. No. 12/135,591, 12 pages.

Final Office Action, dated Nov. 17, 2012, regarding USPTO U.S. Appl. No. 12/135,591, 10 pages.

Notice of Allowance, dated Jul. 6, 201, regarding U.S. Appl. No. 12/135,591, 8 pages.

Office Action, dated Nov. 29, 2010, regarding USPTO U.S. Appl. No. 12/189,293, 12 pages.

Notice of Allowance, dated Apr. 11, 2011, regarding USPTO U.S. Appl. No. 12/189,293, 9 pages.

Office Action, dated Jun. 13, 2011, regarding USPTO U.S. Appl. No. 12/189,293, 11 pages.

Notice of Allowance, dated Nov. 2, 2011, regarding USPTO U.S. Appl. No. 12/189,293, 8 pages.

Office Action, dated Mar. 16, 2012, regarding USPTO U.S. Appl. No. 12/189,288, 12 pages.

Final Office Action, dated Aug. 31, 2012, regarding USPTO U.S. Appl. No. 12/189,288, 16 pages.

Office Action, dated Sep. 8, 2009, regarding USPTO U.S. Appl. No. 12/235,142, 10 pages.

Notice of Allowance, dated Jan. 4, 2012, regarding USPTO U.S. Appl. No. 12/235,142, 7 pages.

\* cited by examiner

REDUCING THE RINGING OF ACTUATOR ELEMENTS IN ULTRASOUND BASED HEALTH MONITORING SYSTEMS

BACKGROUND INFORMATION

1. Field

The present disclosure relates generally to processing data and in particular to processing data from responses of a structure to an input wave form. Still more particularly, the present disclosure relates to a method, apparatus, and computer usable program code for identifying anomalies in a structure.

2. Background

Composite and metallic aircraft structures may be susceptible to internal changes that may occur from fatigue, impacts, and other events or conditions. Composite materials typically have a minimal visual indication of these types of changes. As a result, an aircraft may be inspected to assess the integrity of the structure on a periodic basis or after visual indications of surface anomalies, such as, for example, dents and scratches.

For example, impacts to a structure, such as an aircraft, may occur during cargo loading and unloading. Inspections of the structure of an aircraft may be time-consuming and costly in terms of the time and skill needed to perform the inspection. Further, an airline may incur lost revenues from the aircraft being out of service.

Health monitoring techniques have been developed and used to monitor structures. These techniques often build the health monitoring systems into the structures. These health monitoring systems may be used to determine whether changes have occurred to these materials and structures over time.

Sudden changes in environment, such as, for example, electromagnetic effects, mechanical stresses, and other environmental effects, may affect the integrity of various materials and structures over time. By having health monitoring systems built into or associated with the structures to monitor the structures during use, appropriate measures and responses may be taken to prevent catastrophic failures and prolong the life span of these structures.

The monitoring of structures may include various non-destructive evaluation methods, such as, ultrasonic testing or x-ray testing. Ultrasonic testing uses contact-based transducers to mechanically scan a structure. These distributed sensors and actuators may be surface mounted on the structure or may be embedded in the structure to generate and propagate control of diagnostic signals into the structure being monitored.

A structural health monitoring system is based on using a transmitter and a sensor configuration to transmit waveforms at various frequency ranges and acquire data from the responses. Often times, transducers may function both as a transmitter and a sensor.

Although structural health monitoring systems may provide an automated on board system for detecting and characterizing anomalies or changes that may require maintenance, these types of systems may provide false indications that further inspection and/or maintenance may be needed. These health monitoring systems may have inaccuracies caused by environmental conditions and/or components within the health monitoring systems.

Therefore, it would be advantageous to have a method and apparatus that overcomes the problems described above.

SUMMARY

In one advantageous embodiment, a method is present for monitoring a structure. A signal is sent into the structure, wherein the signal has a limited duration and a varying frequency, wherein the varying frequency varies in a manner to reduce an effect of ringing in the structure. A response to the signal is received and the response is compared to a baseline to form a comparison.

In another advantageous embodiment, an apparatus comprises a structure, a set of transmitters, a set of sensors, and a data processing system. The structure has a set of components. The set of transmitters is physically associated with the set of components, wherein the set of transmitters is capable of sending signals into the set of components. The set of sensors is physically associated with the set of components, wherein the set of sensors is capable of detecting response to the signals. The data processing system is in communication with the set of transmitters and the set of sensors, wherein the data processing system is capable of causing the set of transmitters to send a signal into the structure, wherein the signal has a limited duration and a varying frequency, wherein the varying frequency varies in a manner to reduce an effect of ringing in the structure, receive a response to the signal, and compare the response to a baseline to form a comparison.

In yet another advantageous embodiment, a computer program product comprises a computer recordable storage media and program code for sending a signal into a structure. Program code is present for sending the signal into the structure, wherein the signal has a limited duration and a varying frequency, wherein the varying frequency varies in a manner to reduce an effect of ringing in the structure. Program code is also present for receiving a response to the signal and comparing the response to a baseline to form a comparison.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
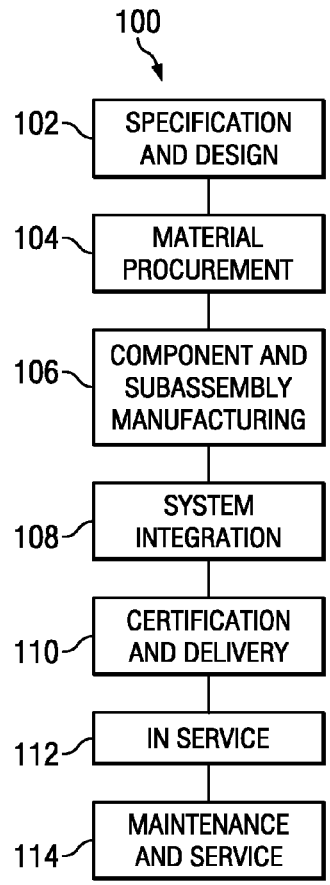
FIG. 1 is a diagram illustrating an aircraft manufacturing and service method in which an advantageous embodiment may be implemented.
Figure 2:
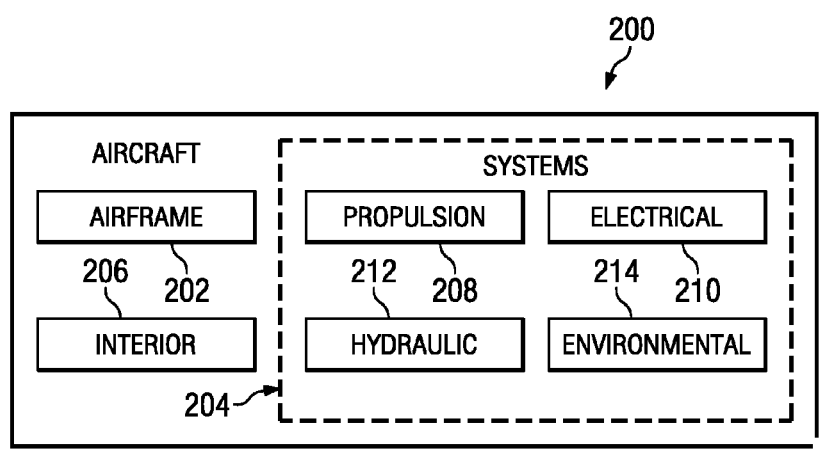
FIG. 2 is a diagram of an aircraft in accordance with an advantageous embodiment.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

In one illustrative example, health monitoring systems of the advantageous embodiments may be implemented during component sub-assembly manufacturing 106 in system integration 108. In other advantageous embodiments, health monitoring systems may be added or implemented during maintenance and service 114. In these different advantageous embodiments, these health monitoring systems may include methods and apparatus for identifying anomalies in a structure in which change indices are identified during monitoring.

Figure 3:
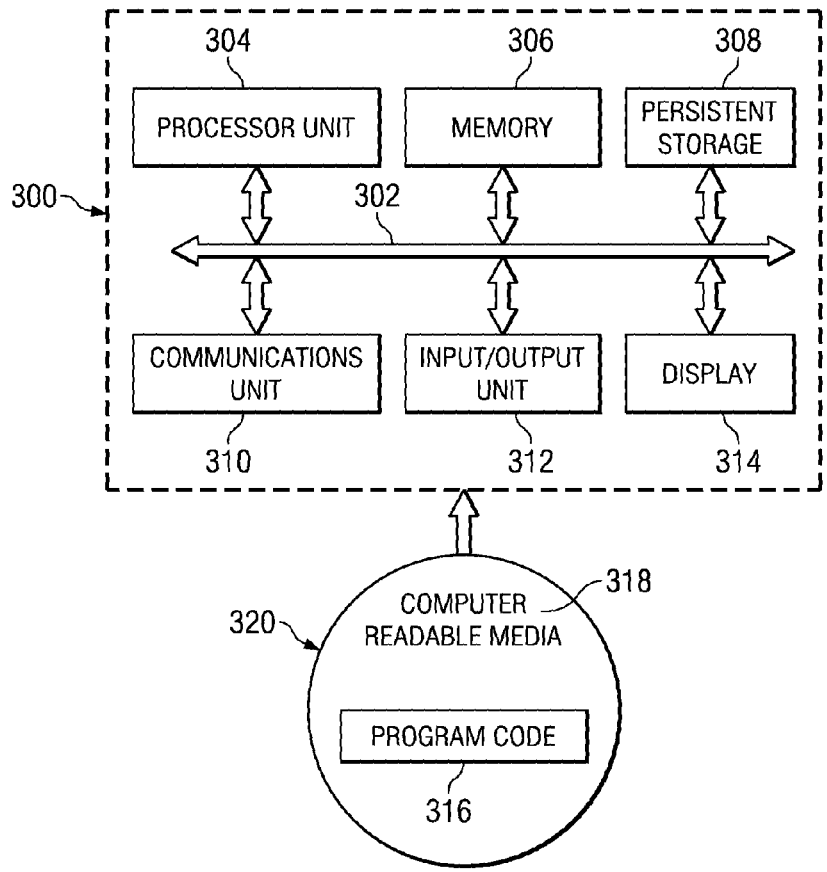
FIG. 3 is a diagram of a data processing system in accordance with an advantageous embodiment.

Turning now to FIG. 3, a diagram of a data processing system is depicted in accordance with an advantageous embodiment. In these examples, data processing 300 may implement processes to identify dissimilarity index in accordance with advantageous embodiments. These change indices may be used to determine whether an anomaly or change is present in a structure. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multiprocessor core, depending on the particular implementation. Further, processor unit 304 may be implemented using one or more heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices. A storage device is any piece of hardware that is capable of storing information either on a temporary basis and/or a permanent basis. Memory 306, in these examples, may be, for example, a random access memory or any other suitable volatile or non-volatile storage device.

Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 316 is located in a functional form on computer readable media 318 that is selectively removable and may be loaded onto or transferred to data processing system 300 for execution by processor unit 304. Program code 316 and computer readable media 318 form computer program product 320 in these examples.

In one example, computer readable media 318 may be in a tangible form, such as, for example, an optical or magnetic disc that is inserted or placed into a drive or other device that is part of persistent storage 308 for transfer onto a storage device, such as a hard drive that is part of persistent storage 308.

In a tangible form, computer readable media 318 also may take the form of a persistent storage, such as a hard drive, a thumb drive, or a flash memory that is connected to data processing system 300. The tangible form of computer readable media 318 is also referred to as computer recordable storage media. In some instances, computer readable media 318 may not be removable.

Alternatively, program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown.

As one example, a storage device in data processing system 300 is any hardware apparatus that may store data. Memory 306, persistent storage 308, and computer readable media 318 are examples of storage devices in a tangible form.

In another example, a bus system may be used to implement communications fabric 302 and may be comprised of one or more buses, such as a system bus, or an input/output bus. Of course, the bus system may be implemented using any suitable type of architecture that provides for a transfer of data between different components or devices attached to the bus system.

Additionally, a communications unit may include one or more devices used to transmit and receive data, such as a modem or a network adapter. Further, a memory may be, for example, memory 306 or a cache such as found in an interface and memory controller hub that may be present in communications fabric 302.

The different advantageous embodiments recognize that structural health monitoring systems may use piezo electric transducers that are bonded or otherwise attached to a structure. During inspections, these transducers may be excited one at a time. The wave forms that propagate may be acquired by all of the sensors in the structure. In a "pitch and catch" mode of operation, all of the transducers, other than the one that is actuated, act as sensors. In a "pulse echo" mode of operation, the transducer transmitting the signal switches to the sensor mode after excitation or transmission of the signal is completed.

One problem that the different advantageous embodiments recognize with the pulse echo systems is that the actuator elements may continue to vibrate for some time after the excitation ends. These continued vibrations may be referred to as residual vibrations. The different advantageous embodiments recognize that the residual vibrations of the actuator element may appear as interference that obscures or drowns out the signal of interest in the acquired waveforms in the response to the signal. This type of interference and/or residual vibration is referred to as "ringing". If the residual vibrations occur at a resonance frequency for the structure, changes or anomalies may be masked by these vibrations. As the residual vibrations are greater, the distance at which anomalies may be masked.

Thus, the different advantageous embodiments provide a method and apparatus for monitoring a structure. A signal is sent into the structure in which the signal has a limited duration and a varying frequency. This frequency may vary over time and may increase or decrease depending on the particular implementation.

The manner in which the frequency varies with time may be selected to reduce residual vibrations. The frequency may be changed such that the frequency ends at a frequency that is far enough away from the resonance frequency to reduce or eliminate residual vibrations that may interfere with identifying anomalies in a structure. In other words the frequency varies in a manner to reduce an effect of ringing in the structure.

More specifically, the effect of ringing is to make it more difficult to detect changes in a structure. In these examples, the effect is the residual vibrations or ringing that may occur. The different advantageous embodiments use a signal that reduces the ringing that may occur. The response to the signal is received and the response is compared to a baseline to form a comparison.

In these examples, the baseline may be a signal, a property of a sensor signal acquired during a test, or some other suitable parameter for comparison. The comparison of the baseline to the response may be a comparison of the signal in the response to the signal in the baseline. In other examples, a property of the signal in the response may be compared to a corresponding property in signal in the baseline. With sinusoidal signals, the instantaneous frequency is typically constant. The comparison may be used to determine whether a change has occurred in the structure.

In these examples, the varying of the frequency is for an instantaneous frequency. An instantaneous frequency may be the time rate of change of the angle of an angle-modulated wave. In other words, an instantaneous frequency may be directly proportional to the time rate of change of an angle of a sine function, the argument of which is a function of time. When the argument is expressed in radians and the time in seconds, the instantaneous frequency may be expressed in hertz in which the time rate of change of the angle is divided by $2\pi$.

The different advantageous embodiments reduce and/or eliminate the ringing effect through the signal with a limited duration and decreasing frequency. In some examples, this decreasing frequency may be a linear decreasing frequency, while in other examples, the decreasing frequency may be a logarithmically decreasing frequency.

Figure 4:
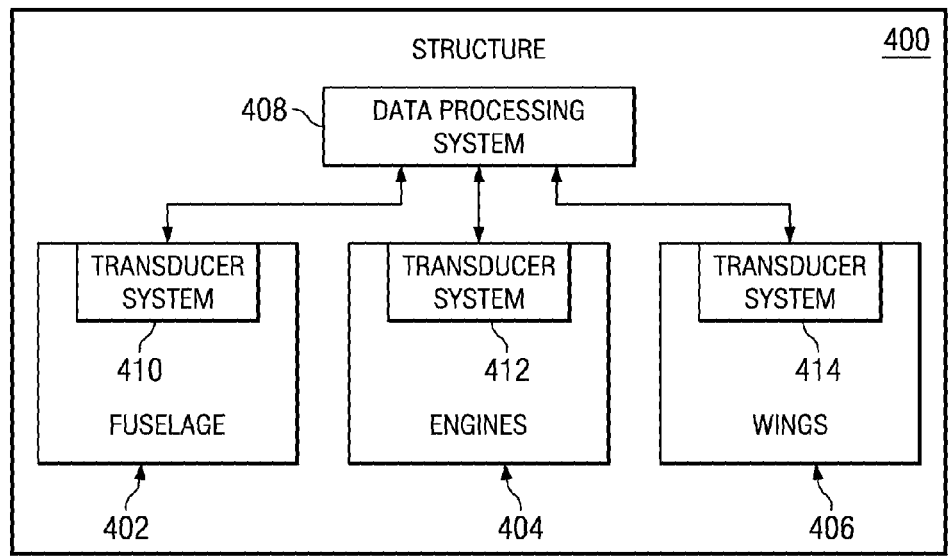
FIG. 4 is a diagram illustrating components used for structural health monitoring in a structure in accordance with an advantageous embodiment.

Turning now to FIG. 4, a diagram illustrating components used for structural health monitoring in a structure is depicted in accordance with an advantageous embodiment. Structure 400 is an example of a structure in which a health monitoring system may be implemented. Structure 400 may take many forms, such as an aircraft, a stationary platform, a land-based structure, an aquatic-based structure, a space-based structure, a mobile platform, or some other suitable object. Specific examples of some of these types of objects include, for example, without limitation, a car, an armored personnel carrier, a surface ship, a submarine, a space station, a dam, a power plant, a bridge, or some other suitable object.

In this example, structure 400 takes the form of an aircraft. Structure 400 includes fuselage 402, engines 404, and wings 406. Other components also may be found in structure 400, but only these depicted ones are presented for purposes of illustrating different features in the different advantageous embodiments.

Structure 400 also includes data processing system 408, transducer system 410, transducer system 412, and transducer system 414. In these examples, data processing system 408, transducer system 410, transducer system 412, and transducer system 414 are for a structural health monitoring system. Although transducers are used for transmitters and sensors, in these examples, any type of transmitter, sensor, or device that is capable of sending and detecting signals at the frequencies needed to transmit the signals into a material may be used.

Data processing system 408 may be implemented in structure 400 using a data processing system, such as data processing system 300 in FIG. 3. Data processing system 408 may take the form of software, hardware, or a combination of software and hardware.

Transducer systems 410, 412, and 414 are examples of transmitters and sensors that may be implemented in structure 400 to transmit signals and detect responses to those signals. In these examples, the transducers in these systems are "associated" with the particular components in structure 400. A transmitter or sensor, such as those in transducer systems 410, 412, and 414, may be physically associated with the component by being attached to the component or even embedded within the component. In these examples, the transducers are fixed transmitters and fixed sensors that are not moved once they are placed. In particular, these transducers may perform or function both as transmitters and sensors.

In this depicted example, transducer system 410 is a set of one or more transducers that is placed onto or within fuselage 402. Transducer system 410 may be attached to surfaces within fuselage 402 or may be embedded into the materials itself, depending on the particular implementation.

The different transducers within transducer system 410 are arranged to be capable of monitoring one or more areas within fuselage 402. These areas may be selected based on different factors, such as identifying areas in which damage may cause a failure within fuselage 402. In a similar fashion, transducer system 412 is attached to or integrated with components in engines 404. Transducer system 414 also is integrated and configured to collect data from one or more areas in wings 406.

Transducer systems 410, 412, and 414 are controlled by data processing system 408. Data processing system 408 may send signals for transmission by these transducer systems. Further, the responses received in response to these signals are returned to data processing system 408 for processing. The responses collected from transducer systems 410, 412, and 414 are compared to a baseline. This comparison may be between the actual signal in a response and a signal in the baseline.

In other advantageous embodiments, a property of a signal in a response may be compared to a corresponding property in the baseline. The property may take various forms for example, the property may be a statistic regarding the response signal, a shape of the signal, a parameter estimated from the signal, or some other suitable property.

In these examples, the transducers within transducer systems 410, 412, and 414 may be operated in different modes. For example, a pitch and catch mode may be used in which all of the transducers, other than the transducer that is selected to transmit the signal, act as sensors. In a pulse echo mode of operation, a transducer may switch from transmitting a signal as a transmitter to receiving a response to the signal as a sensor. In this manner, the transducer may acquire the reflected signals that are returned.

The illustration of structure 400 in FIG. 4 is presented for the purposes of explaining one advantageous embodiment. This illustration is not meant to limit the manner in which different advantageous embodiments may be implemented or embodied. For example, in other advantageous embodiments, other numbers of transducer systems may be present. For example, structure 400 may include five, ten, twenty, or some other suitable number of transducer systems depending on the particular implementation. Also, additional structural health monitoring systems, in addition to data processing system 408, also may be present for redundancy.

Figure 5:
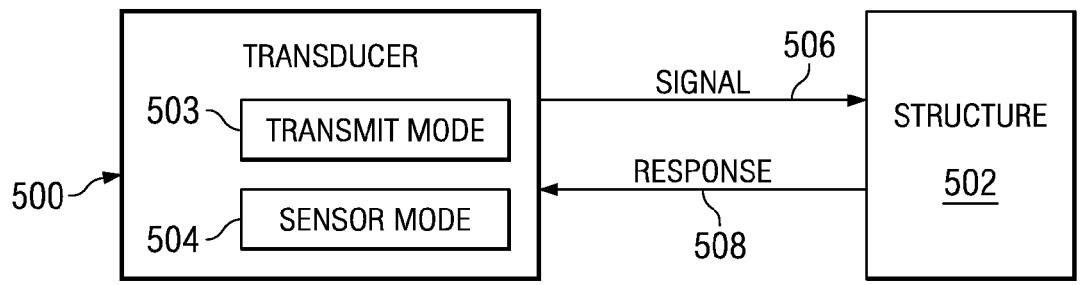
FIG. 5 is a diagram illustrating signal transmission and detection in accordance with an advantageous embodiment.

Turning now to FIG. 5, a diagram illustrating signal transmission and detection is depicted in accordance with an advantageous embodiment. In this example, transducer 500 may be used to test structure 502. Transducer 500 is an example of a transducer that may be found in transducer system 410 in FIG. 4. Structure 502 is an example of a material that may be present in a structure, such as fuselage 402 or wings 406 in FIG. 4.

Transducer 500 may include two modes of operation. In this example, transducer 500 includes transmit mode 503 and sensor mode 504. Transmit mode 503 may be used to transmit or send signal 506 into structure 502 while transducer 500 is in transmit mode 503. Signal 506 is a waveform having a selected frequency range. In these examples, transducer 500 switches from transmit mode 503 to sensor mode 504 after signal 506 is transmitted.

Response 508 is detected by transducer 500 in sensor mode 504. Response 508 is generated in response to the transmission of signal 506 into structure 502. With this configuration, response 508 is detected from reflections or scattering of signal 506 being transmitted into structure 502.

Response 508 is used, in these different illustrative examples, in a comparison with a prior response to determine whether changes have occurred in structure 502. These changes may be anomalies that occur through various stresses and other environmental conditions to which structure 502 is subjected to over time.

The different advantageous embodiments generate signal 506 in a manner that reduces ringing that may occur from sending signal 506 into structure 502. Without signal 506 transmitted in accordance with an advantageous embodiment, as depicted in FIG. 5, residual vibrations and/or interferences referred to as ringing may make it more difficult to detect changes in structure 502. In one example, a waveform may travel at a speed of v km/s. The length of the excitation together with significant residual vibration may be T μs.

With this example, a transducer system, such as transducer system 410 in FIG. 4, using a transducer such as transducer 500 in FIG. 5, may not be able to detect changes in material 502 that are closer to transducer 500 than 0.05 vT cm along the direction of the reflected wave. When the wave velocity is 5 km/s, each microsecond of additional vibration of the actuating element increases the radius of this "blind" area by around 0.25 cm. As described above, the different advantageous embodiments recognize that having a residual vibration at a frequency that is close to or at the resonance frequency may cause a masking or drowning out of the response signal. Such extended vibrations may hide and/or obscure anomalies from detection by the structural health monitoring system that analyzes the corresponding response signals.

This example illustrates the need recognized by the different advantageous embodiments to employ a structural health monitoring system in which the ringing is reduced to a minimum possible duration. In these examples, the approach for ringing mitigation is based on the fact that the duration and strength of the residual vibration of the transducer depends on the actuation frequency. If the actuation frequency is at or near the resonant frequency of the actuator element, the material will experience higher residual vibration, and this situation appears as higher amplitude ringing in the response signal.

The resonance frequency depends on a variety of parameters, including the actuator element properties, the characteristics of the structure to which the element is bonded to, the adhesive properties, and other suitable characteristics. Consequently, one way to mitigate the ringing is to select a frequency of excitation for the signal that is as far away from the resonance frequency as possible and still useful for damage detection. Thus, the different advantageous embodiments recognize that using wideband signals may be helpful in avoiding a situation in which the ringing occurs at a resonance frequency in a manner that masks or obscures changes in the structure.

A wideband signal is a signal that spans a plurality of frequencies. More specifically, a wideband signal may span a range of frequencies. This range may be a continuous range. The frequency values may be such that the difference between a highest frequency and a lowest frequency is large as compared to the mean of all frequencies present in the signal.

Figure 6:
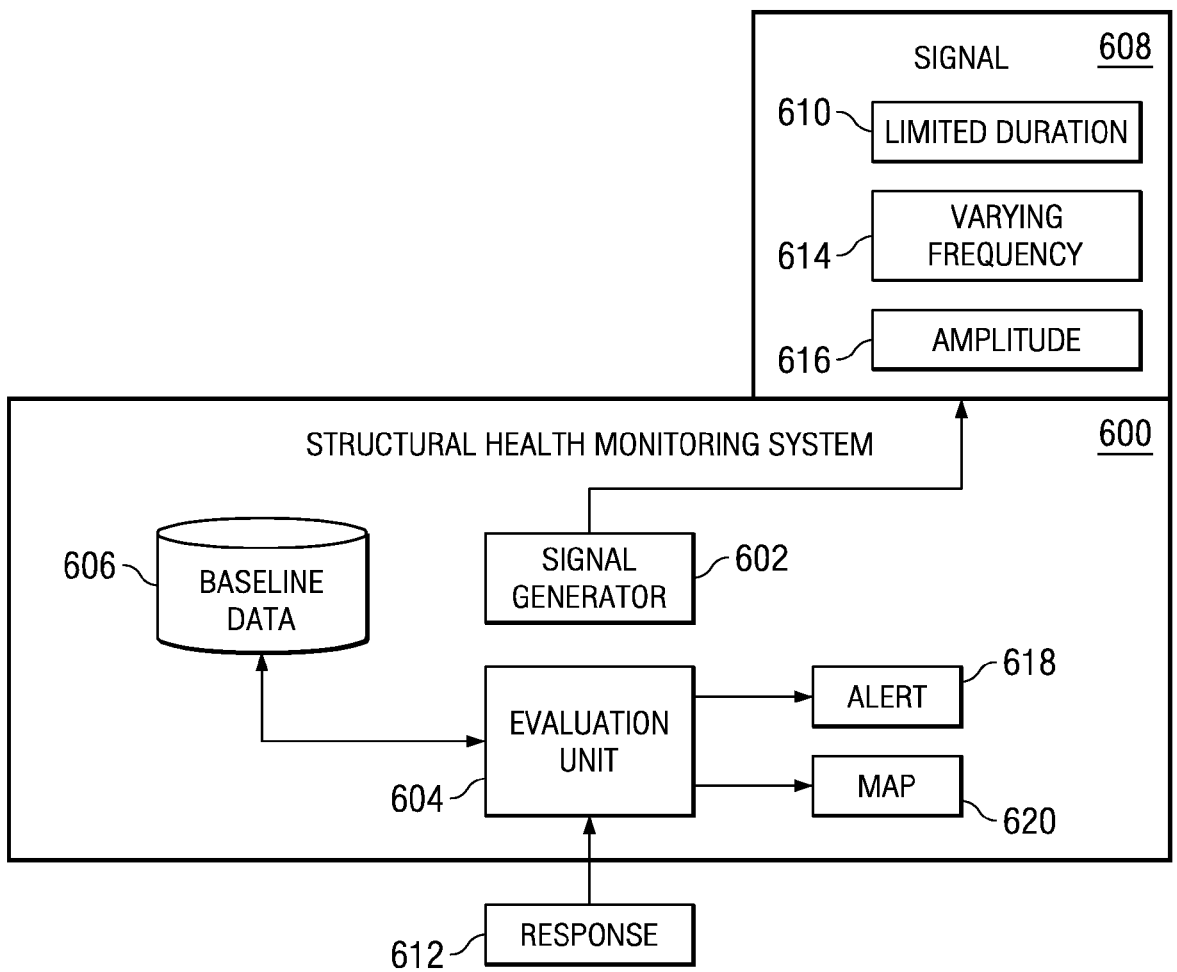
FIG. 6 is a diagram of a structural health monitoring system in accordance with an advantageous embodiment.

With reference now to FIG. 6, a diagram of a structural health monitoring system is depicted in accordance with an advantageous embodiment. In this example, structural health monitoring system 600 is an example of one implementation of structural health monitoring system 408 in FIG. 4. As illustrated, data processing system 600 includes signal generator 602, evaluation unit 604, and baseline data 606.

Signal generator 602 may generate signal 608 for transmission by a transducer such as, for example, transducer 500 in FIG. 5. Signal 608 has characteristics that reduce ringing. Signal 608, in these examples, has limited duration 610. In other words, signal 608 is transmitted for some selected period of time that is shorter than the duration of response 612. Also, signal 608 has varying frequency 614.

Varying frequency 614 may be a linear and/or logarithmically varying frequency in these examples. Varying frequency 614 may be an instantaneous varying frequency. Varying frequency 614 may increase and/or decrease. Varying frequency 614 may be selected such that the ringing is not close enough to the resonance frequency such that an anomaly change in the structure cannot be detected by evaluation unit 604 because of the ringing.

Evaluation unit 604 receives response 612 and may compare response 612 to baseline data 606. In these examples, baseline data 606 may take the form of signals generated in response to interrogating the structure at a prior point in time. These signals also may be referred to as comparison signals. This prior point in time may be a time when the structure was first manufactured. Of course, baseline data 606 may contain signals for other points in time after the creation of the structure. In yet other advantageous embodiments, baseline data 606 may be other values and/or data, such as, for example, without limitation, a property of a signal. This collective data in baseline data 606 may be referred to as a baseline.

Evaluation unit 604 may generate alert 618 if a change is detected based on the comparison of response 612 with baseline data 606. Additionally, evaluation unit 604 may generate map 620. Map 620 may be a map of a location for changes found within the structure. In one example, map 620 may include a two-dimensional or three-dimensional view of the structure along with indications or identifiers of points, regions, or sections within the structure in which changes have been identified.

Figure 7:
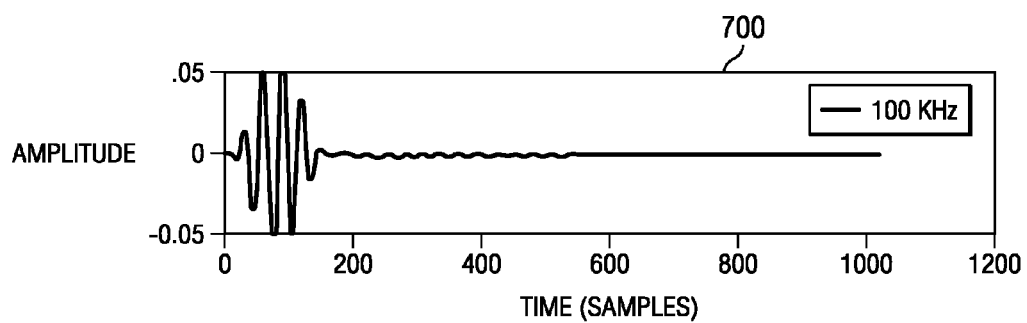
FIGS. 7-10 are diagrams illustrating response signals that may be detected in accordance with advantageous embodiments.
Figure 8:
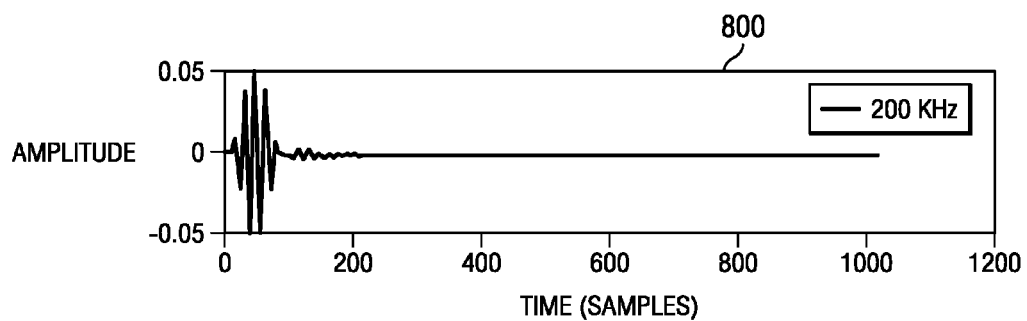
Figure 9:
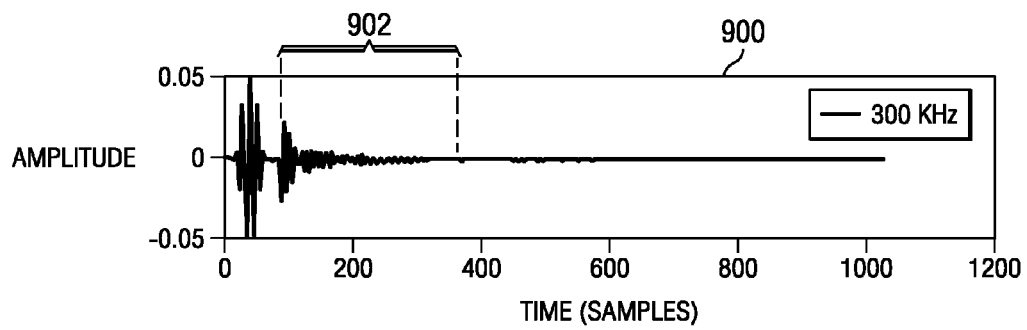
Figure 10:
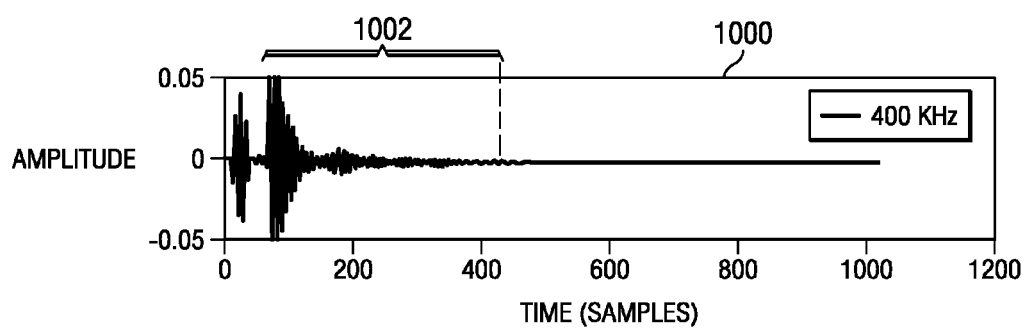

With reference now to FIGS. 7-10, diagrams illustrating response signals that may be detected are depicted in accordance with an advantageous embodiment. In this example, graph 700 in FIG. 7 illustrates a response detected at 100 KHz, graph 800 in FIG. 8 illustrates a response detected at 200 KHz, graph 900 in FIG. 9 illustrates a response detected at 300 KHz, and graph 1000 in FIG. 10 illustrates a response detected at 400 KHz.

The different graphs in these figures are windowed tone signals used to excite the structure. In these examples, the test or excitation signals are windowed tone functions. The responses detected by the sensors are not windowed tone functions. An example of a windowed tone signal is a sine wave extending over a few periods multiplied by a Hann window function. In these examples, the number of periods may be, for example, 3 to 10 periods.

In this example, the resonance frequency for the transducer is between 350 KHz and 450 KHz. The response detected at 200 KHz in graph 800 and 100 KHz in graph 700 show little ringing, while the response in graph 900 shows ringing in section 902 and the response in graph 1000 shows ringing in section 1002. In some advantageous embodiments, selecting a frequency far enough away from the resonance frequency allows for avoiding the ringing illustrated in sections 902 and 1002. For example, data may be acquired for frequencies around 100 KHz and 200 KHz as illustrated in graphs 700 and 800, respectively.

A number of situations may be present in which a wideband excitation of a structure is desirable. Wideband excitation involves the transmission of a signal containing a wide range of frequencies. A chirp signal may be employed when wideband signals are desired. With these types of signals, the resonance frequencies may be unavoidable in some situations.

In another advantageous embodiment, a chirp signal may be such that the instantaneous frequency of the signal increases with time from some low value initially to some other higher value as the stimulation ends. One example of such a signal is the linearly increasing chirp described by the following equation:

$$s(n) = \cos(\phi(n))w(n), \quad (1)$$

where $w(n)$ is a window function and $\phi(n)$ is the instantaneous phase of the stimulus signal as given by $$\phi(n) = \frac{2\pi f_0}{F_s} + \pi \delta, n^2 + \theta, \quad (2)$$

and $\theta$ is an arbitrary constant phase offset that may be set to 0. In equation (2), the frequency $f_0$ represents the instantaneous frequency at the start of excitation, the variable $\delta$ denotes the rate of linear change of the instantaneous frequency given by $$\delta = \frac{f_L - f_0}{F_S(L-1)}, \quad (3)$$

with $f_L$, $F_S$ and L being the instantaneous frequency at the end of the excitation interval, the sampling frequency, and the duration of the excitation interval in a number of samples, respectively.

Figure 11:
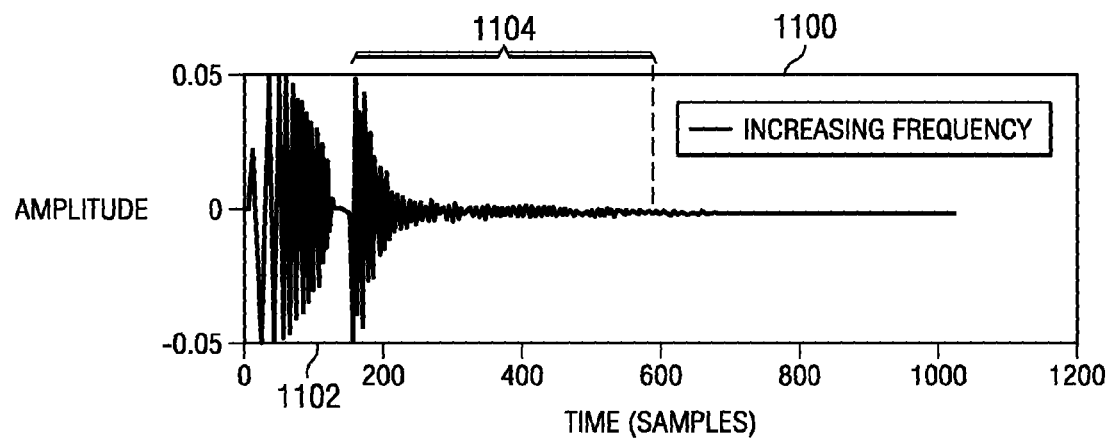
FIGS. 11-12 are diagrams illustrating signals with varying frequency in accordance with an advantageous embodiment.
Figure 12:
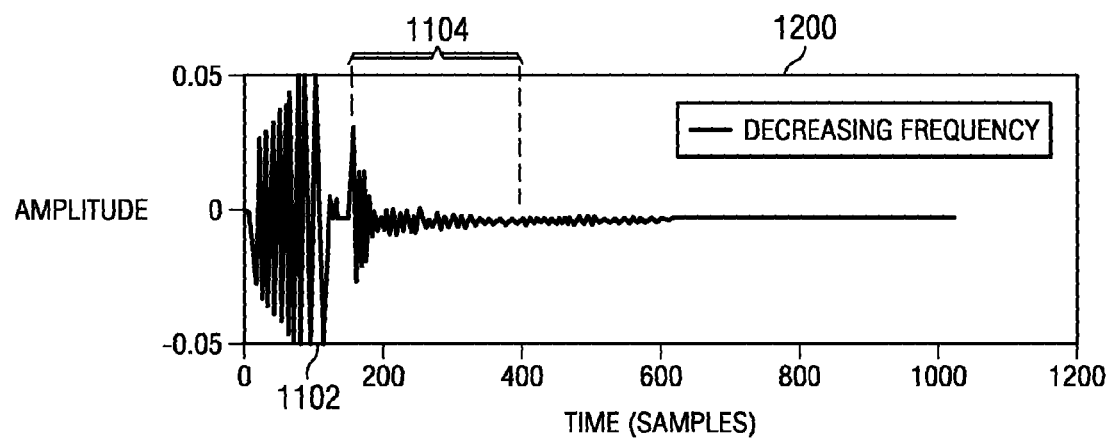

With reference now to FIG. 11 and FIG. 12, diagrams illustrating signals with varying frequency are depicted in accordance with advantageous embodiments. In FIG. 11, graph 1100 illustrates a linearly increasing frequency. In this example, graph 1100 increases in frequency from around 50 KHz to around 600 KHz. The transmitted signal ends at around 1102 with ringing shown in section 1104.

In FIG. 12, graph 1200 illustrates a signal and response with a linearly decreasing frequency. In this example, the transmitted signal ends at around point 1102 with the response beginning after point 1102. As can be seen, in this example, ringing may be seen in section 1104. The ringing in section 1104 is smaller than the signal with increasing frequency in graph 1100. The signal in graph 1200 is a decreasing frequency signal whose instantaneous frequency decreases from around 600 KHz to 50 KHz in this example.

FIGS. 11 and 12 illustrate that a signal may be selected in a manner that the instantaneous frequencies at the end of a signal may be a value away from the resonance frequency. This type of signal selection or design may reduce problems associated with ringing when a health monitoring system operates transducer systems in a pulse echo mode.

One manner in which the residual vibrations may be reduced while keeping the same frequency content in the excitation signal is to rearrange the manner in which the instantaneous frequency changes, such that the frequencies in the vicinity of the resonance frequency of the actuator appear at the start of the excitation.

For example, a linear chirp signal has an instantaneous frequency that decreases from its highest value at the start of excitation to its lowest value at the end of excitation. This linear chirp signal may be sent as signal 506 in FIG. 5. Equation (1) is still valid for this signal; however, since the initial frequency is larger than the final frequency, δ will be negative.

In another advantageous embodiment, a logarithmic chirp signal may be used. This type of signal may be one in which the instantaneous frequency increases at an exponential rate given by $$f(n) = f_a \beta^n, \quad (4)$$

where $f_a$ is the initial frequency and β is given by $$\beta = \frac{1}{L} \log\left(\frac{f_L}{f_0}\right) \quad (5)$$

In this manner, a logarithmic chirp signal may be created using a decreasing frequency by choosing an initial frequency to be higher than the final value of the instantaneous frequency. As a result, β is between 0 and 1 in these illustrative examples. This type of signal may also reduce ringing.

Figure 13:
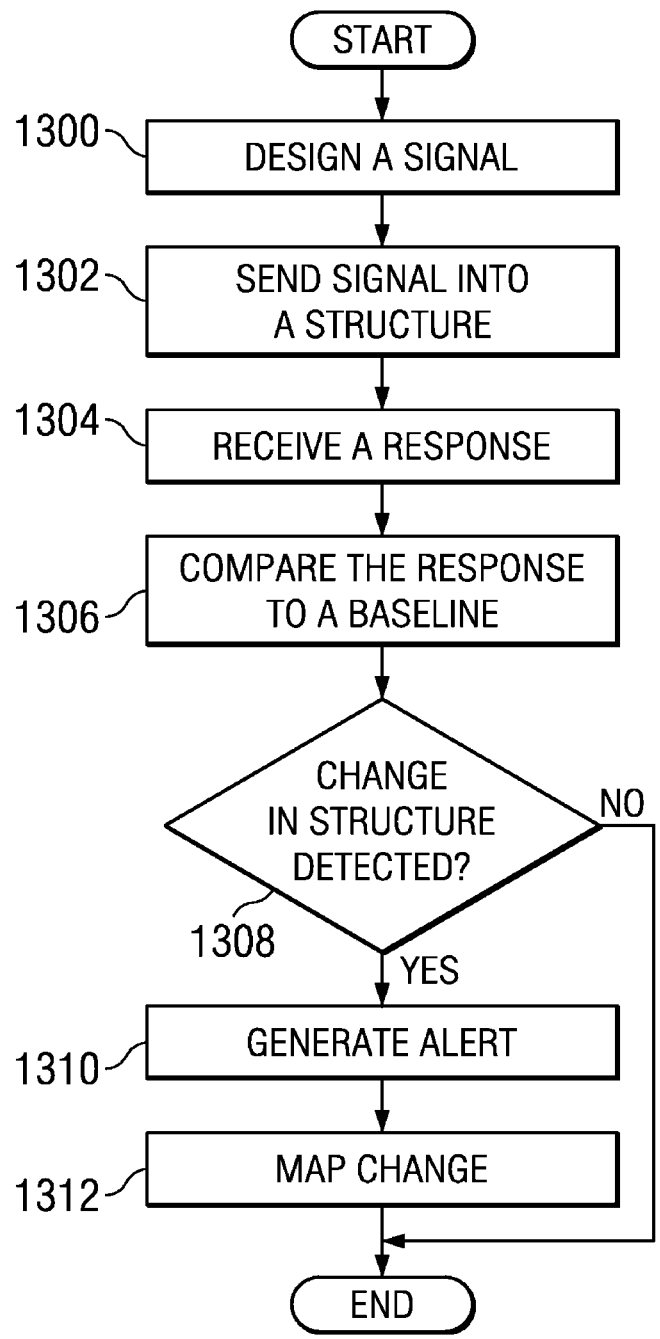
FIG. 13 is a flowchart of a process for monitoring a structure in accordance with an advantageous embodiment.

With reference now to FIG. 13, a flowchart of a process for monitoring a structure is depicted in accordance with an advantageous embodiment. The process illustrated in FIG. 13 may be implemented in a system, such as data processing system 408 in FIG. 4.

The process beings by designing a signal (operation 1300). In operation 1300, the different advantageous embodiments may select a signal in which the frequency varies over time. In these examples, the decreasing frequency may be, for example, without limitation, linear and/or logarithmic.

The process sends the signal into a structure (operation 1302). A response is received (operation 1304). Operation 1302 and operation 1304 may be performed using a single transducer in a pulse echo mode. Of course, these operations may be performed using other modes, such as, for example, a pitch and catch mode. In other embodiments, multiple sensors may receive signals propagated from a single transducer. In other embodiments, several transmitters may send signals to the sensors in a sequential or some other selected order.

The process compares the response to a baseline (operation 1306). A determination is made as to whether a change in the structure is detected based on the comparison (operation 1308). If a change is detected, an alert is generated (operation 1310). This alert may be, for example, a signal or message sent to another component within the health monitoring system. In other advantageous embodiments, the alert may be sent to another component such as, for example, a flight control system in an aircraft. In yet other examples, the alert may be a message sent to a human operator. The process then maps the change in the structure (operation 1312), with the process terminating thereafter.

With reference again to operation 1308, if a change in the structure is not detected, the process terminates. In these examples, the different operations illustrated in FIG. 13 are only examples of some of the operations that may be performed in monitoring a structure. Other operations may be used in place of or in addition to the ones shown in this particular example. Further, different operations may be performed in different sequences depending on the particular implementation.

For example, in some advantageous embodiments, one or both of operations 1310 and 1312 may be eliminated. In other advantageous embodiments, operation 1312 may be performed before operation 1310. In yet other examples, operation 1300 may be unnecessary if a pre-designed or pre-selected signal is used in the health monitoring system.

Thus, the different advantageous embodiments provide a method and apparatus for monitoring a structure. In the different examples, a signal may be sent to the structure in which the signal has a limited duration and a decreasing frequency. A response to the signal is received. This response is compared to a baseline to form a comparison. The comparison may then be used to determine whether a change has occurred in the structure.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer-usable or computer readable medium can generally be any tangible apparatus that can contain, store, communicate, propagate, or transport the program for use by or in connection with the instruction execution system, apparatus, or device.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. An optical disk may include a compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples, such as modems and network adapters, are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art. For example, the different advantageous embodiments are illustrated by comparing the response to a baseline.

Other advantageous embodiments may compare the response to other signals other than a baseline. This baseline may be, for example, a baseline signal that is a response generated from when the structure is in an unaltered or unchanged condition. This signal may be obtained when the structure is first manufactured or at some other point in time. For example, a signal from another time during the monitoring may be used other than the baseline signal. In yet other advantageous embodiments, the baseline may be a property of the signal rather than a signal.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for monitoring a structure, the method comprising:
    sending, by a transmit mode of a transducer embedded in a material of the structure, an electronic signal into the material of the structure, wherein the electronic signal has a limited duration and a varying frequency, wherein the varying frequency varies In a manner to reduce an effect of ringing in the structure by varying over time and ending at a frequency that is at a distance from a resonance frequency of the structure to reduce one or more residual vibrations caused by the electronic signal in the material of the structure;
    receiving, by a sensor mode of the transducer, a plurality of reflections from the material of the electronic signal sent by the transmit mode of the transducer wherein the transducer switches from the transmit mode to the sensor mode after the electronic signal is sent by the transducer; and
    comparing the response to a baseline to form a comparison, wherein the comparison indicates a particular condition of the material.

2. The method of claim 1 further comprising:
    determining whether a change has occurred in the material of the structure using the comparison.

3. The method of claim 2 further comprising:
    responsive to a determination that the change has occurred in the material of the structure, mapping the change.

4. The method of claim 1, wherein the varying frequency is selected from one of an increasing frequency and a decreasing frequency.

5. The method of claim 1, wherein the varying frequency is a linearly varying frequency.

6. The method of claim 1, wherein the varying frequency is a logarithmically decreasing frequency.

7. The method of claim 1, wherein the electronic signal is sent into the material of the structure using a set of transducers operating in a pulse echo mode.

8. The method of claim 1, wherein the structure is selected from one of an aircraft, a building, a dam, a submarine, a spacecraft, a ship, a truck, a tank, a bridge, and a wall.

9. The method of claim 1, wherein the electronic signal is a baseline signal.

\* \* \* \* \*